United States Patent [19]

Babin et al.

[11] Patent Number: 5,364,950

[45] Date of Patent: Nov. 15, 1994

[54] PROCESS FOR STABILIZING PHOSPHITE LIGANDS IN HYDROFORMYLATION REACTION MIXTURES

[75] Inventors: James E. Babin, Hurricane; John M. Maher, Charleston; Ernst Billig, Huntington, all of W. Va.

[73] Assignee: Union Carbide Chemicals & Plastics Technolgy Corporation, Danbury, Conn.

[21] Appl. No.: 953,015

[22] Filed: Sep. 29, 1992

[51] Int. Cl.$^5$ .............................................. C07F 15/00
[52] U.S. Cl. ....................................... 556/2; 558/71; 568/429; 568/444; 568/454
[58] Field of Search ............................. 556/2; 558/71

[56] References Cited

U.S. PATENT DOCUMENTS

| | | | |
|---|---|---|---|
| 3,499,933 | 3/1970 | Pruett et al. | 260/598 |
| 3,553,298 | 1/1971 | Hodan et al. | 558/71 |
| 3,644,446 | 2/1972 | Booth et al. | 260/429 R |
| 4,464,515 | 8/1984 | Rempel et al. | 525/338 |
| 4,482,749 | 11/1984 | Dennis et al. | 568/454 |
| 4,496,768 | 1/1985 | Dennis et al. | 568/454 |
| 4,496,769 | 1/1985 | Dennis et al. | 568/454 |
| 4,503,196 | 3/1985 | Rempel et al. | 525/338 |
| 4,567,306 | 1/1986 | Dennis et al. | 568/455 |
| 4,599,206 | 7/1986 | Billig et al. | 502/85 |
| 4,650,894 | 3/1987 | Fisch et al. | 558/71 |
| 4,668,651 | 5/1987 | Billig et al. | 502/158 |
| 4,712,775 | 12/1987 | Buma et al. | 267/220 |
| 4,714,773 | 12/1987 | Rapoport | 558/338 |
| 4,717,775 | 1/1988 | Billig et al. | 568/454 |
| 4,769,498 | 9/1988 | Billig et al. | 568/454 |
| 4,810,815 | 3/1989 | Bryndza | 558/338 |
| 5,103,033 | 4/1992 | Bank | 556/415 |

FOREIGN PATENT DOCUMENTS

| | | |
|---|---|---|
| 177999 | 4/1986 | European Pat. Off. . |
| 366212 | 5/1990 | European Pat. Off. . |
| 0455261 | 11/1991 | European Pat. Off. . |
| 0455261A1 | 11/1991 | European Pat. Off. . |
| 459464 | 12/1991 | European Pat. Off. . |
| 0348284 | 9/1960 | Switzerland ................ 558/71 |
| 988941 | 4/1965 | United Kingdom . |
| 1198815 | 7/1970 | United Kingdom . |

OTHER PUBLICATIONS

Abu–Hasanayn, F., M. E. Goldman, A. S. Goldman, J. Am. Chem. Soc. 114 (7), 2520, (1992).

King, R. B., Synlett (10), 671 (1991).

Frost, A. A. and R. G. Pearson, *Kinetics and Mechanisms*, John Wiley & Sons Inc., N.Y., 1953, pp. 19–20.

Kosheckima, L. P. and I. P. Mel'nichenko, (Inst. Org. Khim., Kiev, USSR) Ukr. Khim. Zh. (Russ. Ed.), 40(2), 172–4) [Chem. Abstr. 80(23), 132739j, (1974)].

Costisella, B. and H. Gross, "Reaktion von Epoxiden mit Phosphonsäuremonoestern und Phosphonsäuren", J. Prakt. Chem., 317(5), 798–806 (1975).

Atkins, P. W., *Physical Chemistry*, W. H. Freeman and Company, San Francisco, Calif., USA, 1978, pp. 854–856.

Lee, S. B., T. Takata and T. Endo, "N–Benzyl Pyridinium Salts as Useful New Catalysts for Transformation of Epoxides to Cyclic Acetals, Orthoesters, and Orthoscarbonates", Chem. Lett., (11), 2019–22, (1990).

U.S. application Ser. No. 07/911,518 filed Aug. 16, 1992, *Asymmetric Syntheses*.

*Primary Examiner*—Patricia L. Morris
*Assistant Examiner*—Michael G. Ambrose
*Attorney, Agent, or Firm*—E. C. Trautlein

[57] ABSTRACT

This invention provides a process for stabilizing a phosphite ligand against degradation in a homogeneous reaction mixture containing a Group VIII transition metal catalyst and the phosphite ligand, said process comprising adding to the reaction mixture an epoxide in an amount from 0.001 to 5 weight percent based on the total weight of the reaction mixture to reduce the degradation of the ligand.

13 Claims, 1 Drawing Sheet

FIGURE
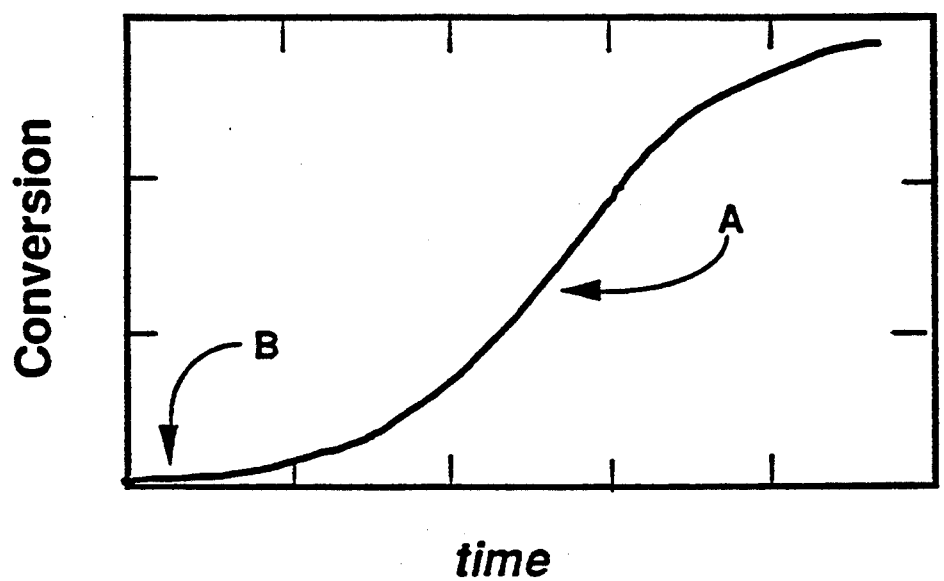

PROCESS FOR STABILIZING PHOSPHITE LIGANDS IN HYDROFORMYLATION REACTION MIXTURES

BACKGROUND OF THE INVENTION

1. Field of the Invention

The present invention is directed to a process for increasing the stability of phosphite ligands that are used for homogeneous catalysis and that are susceptible to degradation. In particular, the invention relates to a process wherein an epoxide is added to a catalyst solution containing s phosphite ligand susceptible to such degradation in order to stabilize the ligand against such degradation.

2. Description of Related Art

In many process, a catalyst is used that comprises s phosphite ligand in combination with transition metal. In particular, the Group VIII metals (such as, but not limited to, cobalt, rhodium, and the like) are utilized in such processes. For example, such catalysts are utilized in processes for hydrogenating unsaturated compounds [such as copolymers of s conjugated diene and co-polymerizable monomer(s)] as disclosed in U.S. Pat. Nos. 4,464,515 and 4,503,196; for oligomerizing or di-merizing olefins as disclosed in European Patent Applications 366212 and 177999; for synthesizing optically-active pharmaceuticals as disclosed in U.S. patent application Ser. No. 911,518, filed Jul. 16, 3992; for hy-drocyanating butadiene to adiponitrile as disclosed in U.S. Pat. Nos. 4,810,815 and 4,714,773; for decar-bonylating aldehydes as disclosed in F. Abu-Hasanayn, M. E. Goldman, A. S. Goldman, J. Am. Chem. Soc. 4 (7), 2520, (1992) and R. B. King, Synlett (10), 671, (1991) and for hydrosilylating olefins as disclosed in U.S. Pat. No. 5,103,033 and in European Application 459464. A particularly important example of such prior art processes is the catalytic hydroformylation of ole-finic compounds with carbon monoxide and hydrogen to produce aldehydes.

Thus, British Patent Specification 988,941 discloses the use as a hydroformylation catalyst comprising a Group VIII transition metal-containing and a biphyllic ligand preferably containing trivalent phosphorus. The phosphorus is combined with any organic group. Typically, the disclosed products are alcohols, although aldehyde products also are contemplated. British Patent Specification 1,198,815 discloses carrying out a hy-droformylation reaction in the presence of cyclic phos-phorus compounds and diphosphines in complexes with cobalt carbonyl.

A rhodium-containing catalyst complex for use in hydroformylation is disclosed in U.S. Pat. No. 3,499,933. The complex is formed with triaryl-phosph-ite, -arsenite, or -bismuthite. Catalyst for hydroformyla-tion of olefins comprising complexes of iridium or rho-dium with biphyllic Group V-A elements, including phosphorous, is disclosed in U.S. Pat. No. 3,644,446. Group VIII transition series metals and poly-phosphite ligands are disclosed for hydroformylation in U.S. Pat. Nos. 4,668,651 and 4,769,498.

Phosphite ligands can be depleted through reaction with components in the hydroformylation reaction mixture. For example, U.S. Pat. No. 4,482,769 postulates the formation of adducts of certain ("open") triorgano-phosphites with the aldehyde products of the hydrofor-mylation reaction. On the other hand, U.S. Pat. Nos. 4,496,768 and 4,496,749 disclose that certain cyclic phosphite ligands are capable of operating for extended periods of time in hydroformylation reaction mixtures with little or no degradation of the ligand.

U.S. Pat. Nos. 4,599,206 and 4,717,775 disclose a mechanism which causes degradation of ligands used in hydroformylations (i.e., autocatalytic decomposition). In this mechanism, the ligands undergo slow hydrolysis in the presence of water in the reaction mixture. The decomposition products then react with aldehyde product and additional water in the reaction mixture in a series of steps to form hydroxyalkylphosphonic acids. The acids so formed catalyze further hydrolysis of the ligand. Such autocatalytic degradation is a multi-step process which produces diverse phosphorus-containing acids, particularly, phosphorous acids. In the presence of water, these phosphorous acids then catalyze hydro-lysis of additional ligand, thus producing additional phosphorous acids. The inevitable "cascade" effect causes hydrolysis of phosphite ligand remaining in the reaction solution to become very rapid and leads to a significant loss of the phosphite ligand.

Such autocatalytic reactions are, in general, well known and are described, for example, in "Kinetics and Mechanisms" by A. A. Frost and R. G. Pearson, John Wiley & Sons Inc., N.Y., 1953, pages 19 and 20. The Figure herein illustrates the increase in concentration of autocatalytic reaction products (e.g., degradation products) with time. Point A in the Figure is the "cascade period", i.e., the period of very rapid, and often virtu-ally uncontrollable, reaction. When the reaction in question is undesirable (e.g., ligand degradation), it is important to maintain the rate of reaction as far below Point A in the Figure as possible, e.g., near Point B.

One method for mitigating degradation of cyclic phosphite ligands used in hydroformylation is disclosed in U.S. Pat. No. 4,567,306. In accordance with this method, a tertiary amine is added to the cyclic ligand that otherwise would degrade by hydrolysis due to ring opening of the cyclic phosphite and the production of acidic materials. The acidic materials catalyze further hydrolysis of the ligand. Tertiary amines reduce ligand destruction by neutralizing the acidic materials and forming ammonium salts. The cyclic ligands used in the method of U.S. Pat. No. 4,567,306 are the ligands dis-closed in above-mentioned U.S. Pat. Nos. 4,496,749 and 4,496,768. However, many amines also catalyze the undesirable condensation of the aldehyde products, thus leading to increased formation of undesirable by-pro-ducts ("heavies") as disclosed by Kosheckima, L. P.; Mel'nichenko, I.V. (Inst. Org. Khim., Kiev, USSR). Ukr. Khim. Zh. (Russ. Ed.), 40(2), 172-4) [Chem. Abstr. 80(23), 132739j, (1974)]. In addition, the above-men-tioned U.S. Pat. No. 4,567,306 discloses that the amines do not halt the decay of the "open" ligands disclosed in above-mentioned U.S. Pat. No. 4,496,769.

Ion-exchange methods also have been utilized in an attempt to control acidity and so reduce phosphite li-gand degradation. One such method is disclosed in above-mentioned U.S. Pat. Nos. 4,599,206 and 4,712,775. In the method of the latter patents, au-tocatalytically-produced phosphonic acid by-products are removed from a liquid reaction mixture containing ligand, hydroformylation catalyst and hydroformyla-tion reactants by passing a portion of the mixture over weakly-basic ion exchange resin to remove the unde-sired acid and the recycling the treated mixture so to the reactor. However, this treatment with ion-exchange resin requires that at least a portion of the catalyst solution be removed from the reactor and treated in an ion-exchange resin bed. Thus, this method requires more catalyst to provide a desired catalyst concentration in the reactor and increases risk of catalyst loss. In addition, a significant additional equipment is required to utilize this method.

The above-described phosphite ligand decomposition products include acidic phosphorous-containing materials. B. Costisella, H. Gross, J. Prakt. Chem., 317(5), 798–806 (1975) ("Costisella Article") discloses the reaction of epoxides and phosphonic acids (alone or in an inert diluent) to produce phosphonate esters by four methods (identified as "Methods A, B, C and D" in the Costisella Article). The epoxides and acids are present in relatively high concentration in the solvent-free reaction mixtures of Methods B and D and in unspecified concentrations in the solvent-containing reaction mixtures of Methods A and C. There is no indication in the Costisella Article of the reaction rate of the epoxide and the acid at low concentrations or of the stability of such ester products against degradation to form acidic by products. It is known from "Physical Chemistry" by P. W. Atkins, W. H. Freeman and Company, San Francisco, Calif., USA, 1978 that reaction rates of non-ionic reactions (such as the reaction disclosed in the Costisella Article) decrease markedly with significant decreases in the concentration of reactants. Hence it would not be obvious from the Costicella Article that low concentrations of epoxides would effectively react with low concentrations of phosphorous acids, particularly in light of the possible competing reaction disclosed in the Lee Article described below.

The above-described hydroformylation processes produce aldehydes. S. B. Lee, T. Takata, T. Endo, Chem. Lett., (11),2019–22, (1990) ["Lee Article"] disclose that, in the presence of catalytic amount of a weak acid, the reaction of epoxides with aldehydes, ketones, lactones, and carbonates produce the corresponding cyclic acetals, orthoesters, and orthocarbonates. The disclosure of the Lee Article suggests that epoxides would react with the aldehyde product in a hydroformylation reaction mixture.

European Pat. No. Application 0 455 261 A1 discloses a process for producing a 1,3-diol (e.g., 1,3-propanediol) and/or a 3-hydroxyaldehyde (e.g., 3-hydroxypropionaldehyde) which comprises contacting an epoxide, carbon monoxide and hydrogen in the presence of a rhodium-containing catalyst composition effective to promote the hydroformylation of the epoxide at conditions effective to form at least one of a 1,3-diol and a 3-hydroxyaldehyde. The rhodium-containing catalyst composition comprises an anionic rhodium-containing complex. Among the rhodium-containing catalysts employed are those having a phosphite ligand. The epoxide may be present in widely varying amounts, for example, in the range of about 0.01% to about 95%, preferably about 0.5% to about 75%, by weight based on the total weight of reactants, catalyst and liquid medium present during this step. In one embodiment, the epoxide hydroformylation occurs in the presence of an electrophile, e.g., $H^+$ ions, protonic acids, Lewis acids and the like and mixtures thereof, in particular, $H^+$ ions in an amount effective to further promote the hydroformylation of the epoxide. The molar ratio of acid to rhodium may be in the range of about 0.1 to about 10, preferably about 0.2 to about 10, preferably about 0.2 to about 3. There is no disclosure in this European patent application of the use of an epoxide as an additive (as distinguished from using an epoxide as a principal reactant) or of stabilizing phosphite ligands against degradation by using an epoxide or of the detrimental effects of acids on phosphite ligands.

SUMMARY OF THE INVENTION

This invention provides a process for stabilizing a phosphite ligand against degradation in a homogeneous reaction mixture (other than an epoxide hydroformylation reaction mixture) containing a Group VIII transition metal catalyst and the phosphite ligand, said process comprising adding to the reaction mixture an epoxide in an amount from 0.001 weight percent to 5 weight percent, based on the total weight of the reaction mixture, to reduce the degradation of the ligand.

BRIEF DESCRIPTION OF THE DRAWING

The FIGURE shows the increase in the concentration of phosphite ligand degradation products with time during the autocatalytic decomposition of ligands.

DETAILED DESCRIPTION OF THE INVENTION

The phosphite ligand-containing transition metal catalysts to which the process of the present invention is applicable are used to promote and catalyze a number of reactions. For example, such catalysts are used to catalyze hydrogenation of unsaturated compounds, such as copolymers of a conjugated diene and co-polymerizable monomers; carbonylation of alkanols to alkanoic acids (e.g., methanol to acetic acid); oligomerization or dimerization of olefins; hydrocyanation of dienes (e.g., the butadiene to adiponitrile); decarbonylation of aldehydes; and hydrosilylation of olefins. This invention is particularly applicable to catalysts used in the hydroformylation of olefins to produce aldehydes.

For convenience, details of the process of the present invention are, to some extent, described herein in particular as they relate to catalysts used in the hydroformylation of olefins to form aldehydes. However, the invention is not limited to the stabilization of phosphite-containing catalysts utilized in olefin hydroformylation. Rather, the invention is also related to various other reaction mixtures for homogeneous catalysis where there exists a need to reduce the degradation of phosphite ligand-containing catalysts.

The phosphite ligands useful in the process of the present invention contain at least one trivalent phosphorus atom, each valence of which phosphorus atom bonds the phosphorus atom to a carbon atom of an organic radical through an oxygen atom. Examples of such ligands include triorganophosphites, diorganophosphites and bis-phosphites. Such phosphite ligands are well known in the art.

For reasons of convenience and not by way of limitation, suitable phosphite ligands stabilized by the method of the present invention include:

(i) poly-phosphites having the formula:

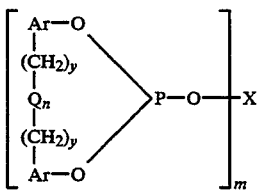

wherein:
(1) Ar represents an identical or different aryl group;
(2) X represents an m-valent hydrocarbon radical selected from the group consisting of alkylene, alkylene-oxy-alkylene, aryl and aryl-$(CH_2)_y$—$(Q)_n$—$(CH_2)_y$-aryl groups;
(3) each y individually has a value of 0 or 1;
(4) each Q individually represents a divalent bridging group selected from the class consisting of —$CR^1R^2$—, —O—, —S—, —$NR^3$—, —$SiR^4R^5$—, and —CO—;
(5) $R^1$ and $R^2$ each individually represents a group selected from the group consisting of hydrogen, alkyl of 1 to 12 carbon atoms, phenyl, tolyl and anisyl groups;
(6) $R^3$, $R^4$, and $R^5$ each individually represents —H or -an alkyl group 3;
(7) each n individually has a value of 0 to 1; and
(8) m has a value of 2 to 6;
(ii) diorganophosphites having the formula:

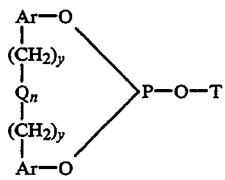

wherein T represents a monovalent hydrocarbon group; and wherein Ar, Q, n and y are as defined above; and
(iii) open ended bis-phosphites having the formula:

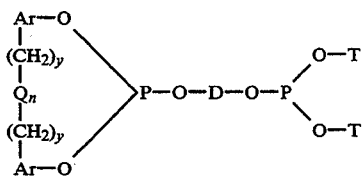

wherein D represents a divalent bridging group selected from the group consisting of alkylene, alkylene-oxy-alkylene, aryl, and aryl-$(CH_2)_y$—$Q_n$—$(CH_2)_y$-aryl and wherein Ar, Q, n, y and to are as defined above and each to may be identical or different; and
(iv) "open" triorganophosphites having the formula:

$(R°O)_3P$     (IV)

wherein R° is a substituted or unsubstituted monovalent hydrocarbon radical.

Illustrative radicals represented by R° in formula (IV) above include aryl, alkaryl, aralkyl, alkyl, cycloalkyl, alkoxyaryl, hydroxyaryl, alkoxyalkyl, and hydroxyalkyl radicals. Representative radicals R include phenyl, naphthyl, o-tolyl, 2-ethylphenyl, 2,6-dimethylphenyl, 4-t-butylphenyl, 4-iso-pentylphenyl, nonylphenyl, benzyl, 2-phenylethyl, 4-phenylbutyl, methyl, ethyl, n-propyl, iso-propyl, n-butyl, sec-butyl, t-octyl, n-decyl, iso-decyl, n-dodecyl, cyclohexyl, cyclopentyl, 4-methylcyclohexyl, p-methoxyphenyl, p-hydroxyphenyl, 2-ethoxyethyl, 2-hydroxyethyl, and the like.

The preferred ligand within the scope of formula (IV) above is triphenyl phosphite. Other suitable ligands within t he scope of formula (IV) include methyl diphenyl phosphite, tricyclohexyl phosphite, tri-o-tolyl phosphite, tri-(2-ethylphenyl) phosphite, tri-(2,6-dimethylphenyl) phosphite, di-iso-decyl phenyl phosphite, tri-(nonylphenyl) phosphite and the like.

Ionic derivatives of such phosphites also may also be used as the phosphite ligands in the process of the present invention. Such ionic phosphites typically have one or more ionic moieties, such as carboxylate or sulfonate, substituted on an aryl moiety of Ar in the proceeding formulas.

Specific illustrative examples of the bisphosphite ligands employable in this invention include such preferred ligands as:

6,6'-[[3,3'-bis(1,1-dimethylethyl)-5,5'-dimethoxy [1,1'-biphenyl]-2,2'-diyl]bis-dibenzo[d,f] [1,3,2]dioxaphosphepin ligand having the formula:

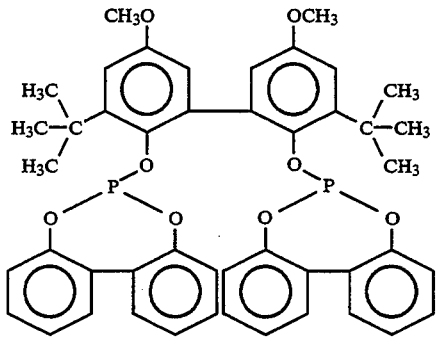

6,6'-[3,3',5,5'-tetrakis(1,1-dimethylpropyl) 1,1'-biphenyl-2,2'-diyl]bis(oxy)]bis-dibenzo[d,f] [1,3,2]-dioxaphosphepin ligand having the formula:

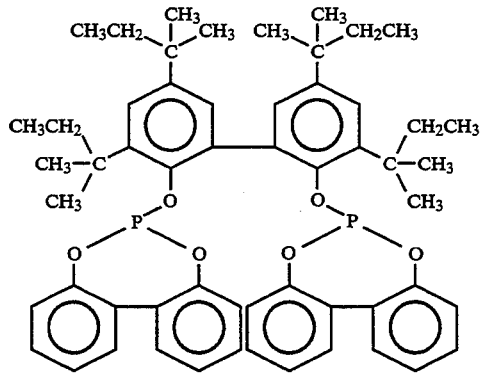

6,6'-[3,3',5,5'-tetrakis(1,1-dimethylethyl) 1,1'-biphenyl-2,2'-diyl]bis(oxy)]bis-dibenzo[d,f] [1,3,2]-dioxaphosphepin ligand having the formula:

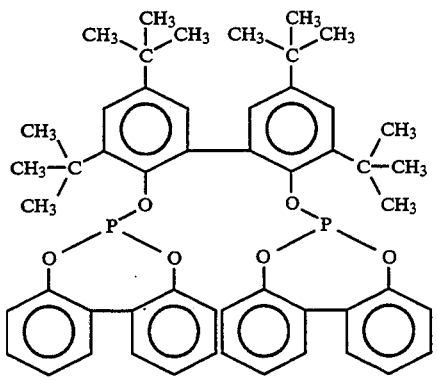

LIGAND A

Typically, the phosphite ligand concentration in hydroformylation reaction mixtures used in the process of the present invention is between about 0.005 and 15 weight percent based on the total weight of the reaction mixture. More usually, the ligand concentration is between 0.001 and 10 weight percent, and most often is between about 0.05 and 5 weight percent on that basis.

The process of this invention is suitably utilized to stabilize phosphite ligands employed to modify catalysts comprising Group VIII transition metals, including ruthenium, rhodium, cobalt, and nickel, often are modified with phosphite ligands and utilized in homogeneous catalysis, such as oligomerization and dimerization of olefins, hydrocyanation, decarbonylation, and hydroformylation. A particularly important representative example of such processes is hydroformylation of olefinic compounds with carbon monoxide and hydrogen in the presence of catalyst comprising ruthenium, rhodium or cobalt or blends thereof, to produce aldehydes.

Typically, the concentration of the Group VIII transition metal in the reaction mixture used in the present invention is up to about 1000 parts per million by weight based on the weight of the reaction mixture, more typically is between about 50 and 750 parts per million by weight based on the weight of the reaction mixture, and most typically is between about 70 and 500 parts per million by weight based on the weight of the reaction mixture.

Epoxides suitably utilized in the process of the present invention include the epoxides having the formulas set forth below. The first such formula is as follows:

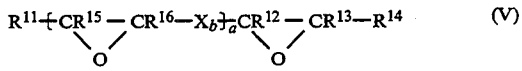

wherein:
(1) a is 0 or 1;
(2) b is 0 or 1;
(3) $R^{11}$, $R^{12}$, $R^{13}$, $R^{14}$, $R^{15}$ and $R^{16}$ are independently selected from the group consisting of hydrogen; monovalent hydrocarbon radicals (such as alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$, $R^{12}$, $R^{13}$, $R^{14}$, $R^{15}$ and $R^{16}$ are linked together to form a cyclic structure which has up to about 30 carbon atoms and which may comprise a plurality of ring structures such as bicyclo-, tricyclo-, tetracyclo- and n-cyclo- groups;
(4) X is a divalent bridging group selected from the group consisting of substituted or unsubstituted alkylene, arylene, aralkylene, and alkarylene groups having up to about 30 carbon atoms, —O—, —S—, —$NR^{19}$—, —$SiR^{20}R^{21}$—, and —CO— and wherein each radical $R^{19}$, $R^{20}$, and $R^{21}$ individually represents H or alkyl groups.

In this definition, the word "substituted" denotes presence of groups which do not react with epoxides, such as alkoxy and aryloxy groups. Excluded from the definition of "substituted" are halogens, carboxyl moieties, nitrile groups, and any other moieties which react with epoxides. Hydrocarbon epoxides generally are preferred.

When a equal 0 and b equal 0 in formula (V) above, epoxides suitable used in the process of this invention have the formula:

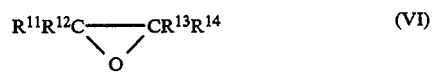

wherein $R^{11}$, $R^{12}$, $R^{13}$, and $R^{14}$ are as described above with regard to formula (V). Examples of suitable epoxides of formula (VI) include, but are not limited to, 1,2-cyclohexene oxide; styrene oxide; propylene oxide; 1,2-octene oxide; 1,2-decene oxide; 1,2-dodecene oxide; 1,2-hexadecene oxide; 1,2-octadecene oxide; ethylene oxide; 1,2-cyclododecene oxide; stilbene oxide; isobutylene oxide; 2,3-epoxybutane; 1,2-epoxybutane; 1,2-epoxyhexane; cyclopentene oxide; cyclooctene oxide; cyclodecene oxide; and 1,2-epoxy-3-phenoxy-propane. Preferably $R^{11}$ and $R^{12}$ in formula (VI) are hydrogen.

Epoxy compositions of formula (VI) above having at least one ring in a cyclic structure formed by the combination of one of $R^{11}$ and $R^{12}$ groups with one of $R^{13}$ and $R^{14}$ groups include cyclic structures which have a plurality of rings associated therewith, including bicyclo- and other n-cyclo- groups. Bicyclo-groups are cyclic hydrocarbon groups consisting of two rings only having two or more atoms in common. Tricyclo-, tetracyclo-, and other n-cyclo- compounds also are included within the definition of cyclic structures having a plurality of rings. Examples of such plural ring structures within the scope of a cyclic structure formed by the combination of one of $R^{11}$ and $R^{12}$ groups with one of $R^{13}$ and $R^{14}$ groups include the bicyclo- compounds norbornane which is also known as bicyclo[2.2.1]heptane and α-pinene which is also known as 2,7,7-trimethyl-Δ²-bicyclo [1.1.3]heptene. Epoxy compounds suitable for use in the subject invention which are formed from norbornane and -pinene are 2,3-epoxynorbornane which is also known as 2,3-epoxy-bicyclo[2.2.1]heptane) and α-pinene oxide.

Epoxy compounds useful in the process of this invention include those having a composition of formula (VI) above, wherein the $R^{11}$ and $R^{12}$ groups together or the $R^{13}$ and $R^{14}$ groups together, or both, may form cyclic structure(s) which may include a plurality of rings. The cyclic structure of such compounds can include bicyclo-, tricyclo-, and other n-cyclo compounds. Nopinene, which is also known as β-pinene or 7,7-dimethyl-2-methylenenorpinane, is a composition having a ring structure which yields an epoxy compound useful in the present invention. The epoxy compound derived from nopinene, β-pinene oxide, is a compound of formula (VI) above wherein $R^{11}$ and $R^{12}$ form a cyclic structure having a plurality of ring structures, $R^{13}$ is a methyl group, and $R^{14}$ is hydrogen.

Diepoxides also are useful in the method of the invention. Suitable diepoxy compounds of formula (VI) include 1,3-butadiene diepoxide, 1,2,7,8-diepoxyoctane, diepoxycyclooctane, dicyclopentadiene dioxide, and 3,4-epoxy cyclohexyl methyl-3,4-epoxy cyclohexyl carboxylate (available as ERL-4221®, a trademark of Union Carbide Chemicals and Plastics Technology Corporation).

The quantity of epoxide utilized in accordance with the process of this invention is that quantity sufficient to interact with the phosphorous acids which cause degradation of phosphite ligand-containing catalysts. Preferably, the quantity of epoxide is sufficient to maintain the concentration of acidic by-products below the threshold level which causes rapid degradation of the ligand (e.g., near point B in the FIGURE). This preferred quantity of epoxide is the quantity which ensures that any degradation of the ligand proceeds by the "non-catalytic mechanism" as described in "The Kinetic Rate Law for Autocatalytic Reactions" by Mata-Perez et al, Journal of Chemical Education, Vol. 64, No. 11 November 1987, pages 925 to 927 rather that by the "catalytic mechanism" described in that article. Most preferably, the quantity is sufficient to maintain the concentration of acidic catalysts at an essentially undetectable level.

A suitable concentration of epoxide in a hydroformylation reaction mixture used in the present invention typically is at least about 0.001 weight percent of the total weight of reaction mixture. Typically, the maximum epoxide concentration is limited by practical considerations, such as the cost of epoxide and by the undesirable side effects of too much epoxide (e.g., the formation of acetal and polyether byproducts and the possible contamination of the desired product with excess epoxide). Although the maximum epoxide concentration is not narrowly limited for the purpose of this invention, a maximum epoxide concentration in practice typically does not exceed about 5 weight percent of the total weight of the reaction mixture. The concentration of epoxide preferably at least about equals, and more preferably somewhat exceeds, a stoichiometric concentration required for the epoxide to interact with each phosphorous acid molecule produced during phosphite degradation. Typically, one epoxide group is required to interact with each phosphorous acid molecule. An excess of epoxide typically is not harmful and a stoichiometric deficiency of epoxide merely limits the effectiveness of the invention. Preferably, the epoxide concentration is maintained between about 0.01 and 2 weight percent based on the total weight of reaction mixture. Most preferably, the epoxide concentration is maintained between about 0.1 and 1 weight percent based on total weight of reaction mixture.

In the process of the present invention, the epoxide is added to and thoroughly mixed into the reaction mixture using any convenient procedure. The epoxide can be mixed with or dissolved in any of the reactant streams or solvent make-up streams or the epoxide periodically can be separately added to the reactant mixture. The epoxide can be added reaction mixture in small quantity over an extended period of operation. In this way, a concentration of epoxide effective to stabilize ligand during steady-state operation is obtained, with epoxide consumed by reaction with phosphorous acid as it is formed. The epoxide also can be added intermittently at a higher concentration, with the intent of achieving a long-term stabilization effect by starting at a higher-than-necessary concentration and allowing the concentration to fall to a more typical concentration during a period without injection addition.

Organic solvents typically used in homogeneously-catalyzed reaction mixtures include saturated hydrocarbons, aromatic hydrocarbons, ethers, aldehydes, ketones, nitriles and aldehyde condensation products. Such solvents may be present in the reaction mixtures used in the present invention and include, but are not limited to, pentanes, cyclohexane, benzene, xylene, toluene, diethyl ether, butyraldehyde, valeraldehyde, acetophenone, cyclohexanone, benzonitrile and Texanol® (2,4,4,-trimethyl-1,3-pentanediol monoisobutyrate).

Without wishing to be bound by any particular theory, it appears that, in the process of the present invention, the epoxide reacts with the phosphorous acids resulting from phosphite degradation and that reaction lowers the concentration of phosphorous acids and correspondingly reduces the formation of additional autocatalytically-produced phosphorous acids. In particular, it appears that the epoxide reacts with the phosphorus acids in accordance with the sequence of reactions that can be illustrated as follows:

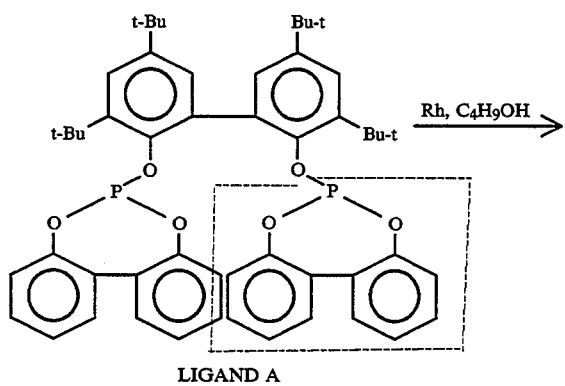

LIGAND A

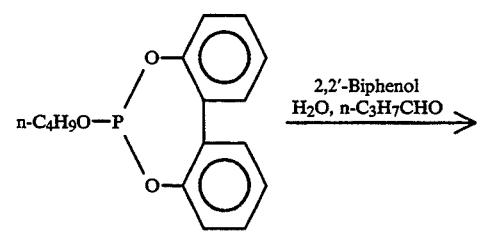

Poisoning Phosphite

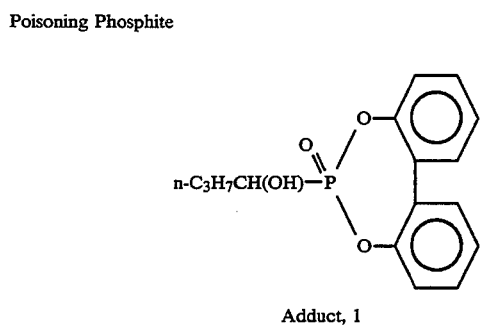

Adduct, 1

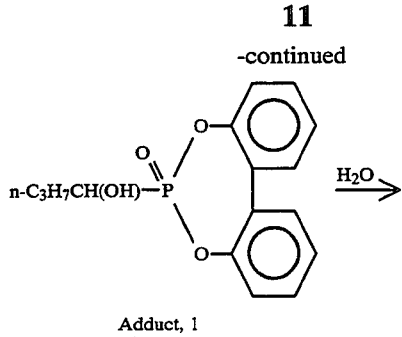

Adduct, 1

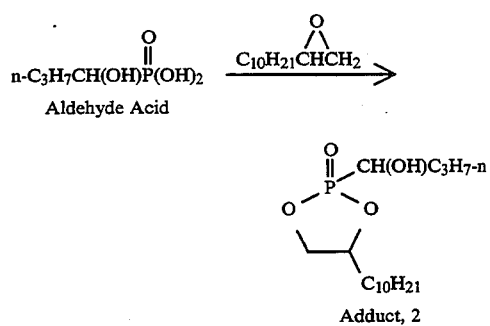

Aldehyde Acid

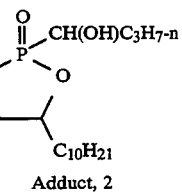

Adduct, 2

The present invention is believed to operate by converting such aldehyde acids to relatively inert adducts (e.g., Adduct 2 in the above reaction sequence).

Regardless of the specific mechanism involved ligand stabilization in the practice of the process of the present invention, the use of epoxides in accordance with this invention reduces the acidity of the reaction mixtures employed in this invention. Thus, in the practice of the process in the present invention, it is preferred to minimize the molar ratio of any acid to the transition metal in the reaction mixture (particularly by the use of an epoxide additive) so that the ratio is no greater than 2.5:1, more preferably no greater than 0.5:1 and most preferably no greater than 0.05:1. Since acids are desirable in the hydroformylation of epoxides, the reaction mixtures used in the process of the present invention do not include the reaction mixtures used in the hydroformylation of epoxides, e.g., the reaction mixtures described in above-mentioned published European Patent Application 0 455 261 A1. (i.e., reaction mixtures containing an epoxide, carbon monoxide and hydrogen as the principal reactants).

Another problem has been observed when phosphite ligand-promoted rhodium catalysts are employed in olefin hydroformylation processes (i.e., the loss in catalytic activity over time during the course of continuous use of such rhodium-phosphite complex catalysts). This loss of catalytic activity can occur even in the absence of extrinsic poisons such as chloride or sulfur compounds. This "intrinsic" loss in catalytic activity observed when phosphite ligand-promoted rhodium catalyst systems are employed is believed to be at least partially due to the formation of phosphite by-products which can be described as decomposition products of the phosphite ligands. When diorganophosphite ligands are used, the by-products consist of alkyl [1,1'-biaryl-2,2'-diyl] phosphites in which the alkyl radical corresponding to the particular n-aldehyde produced by the hydroformylation process and the [1,1'-biaryl-2,2'-diyl] portion of the phosphite being derived from the organobisphosphite ligand employed. Such by-products are illustrated by the "poisoning phosphite" shown in the above reaction sequence. For example, the organobisphosphite ligand employed in the continuous hydroformylation process of propylene in Example 14 of U.S. Pat. No. 4,769,498 (referred to as a poly-phosphite ligand in that Example) will, over the course of the continuous hydroformylation process, experience an intrinsic decrease in catalytic activity because of the formation of n-butyl [1,1'-biphenyl-2,2'-diyl] phosphite. Such alkyl [1,1'-biaryl-2,2'-diyl] phosphites can coordinate with the rhodium metal and form complexes that are less reactive than organobisphosphite ligand-promoted rhodium catalysts. In effect, such alkyl [1,1'-biaryl-2,2'-diyl] phosphites act as catalyst poisons or inhibitors, and lower the catalyst activity of organobisphosphite ligand-promoted rhodium catalysts.

The effect of such poisoning phosphites is reduced or eliminated by the practice of the process of the U.S. patent application being filed concurrently herewith, entitled Improved Hydroformylation Process (assignee's Docket 16997). The latter process is an improved continuous hydroformylation process for producing aldehydes which comprises reacting an olefinically unsaturated compound with carbon monoxide and hydrogen in the presence of a solubilized rhodium-bisphosphite complex catalyst wherein the bisphosphite ligand of said complex catalyst is a ligand selected from the class consisting of:

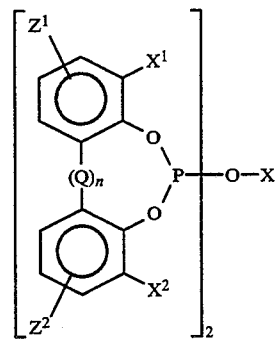

and

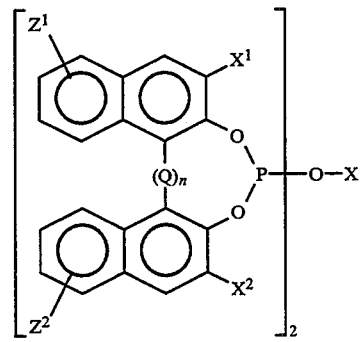

wherein each $X^1$ and $X^2$ radical individually represents a radical selected from the group consisting of hydrogen, methyl, ethyl and n-propyl; wherein each $Z^1$ and $Z^2$ radical individually represents hydrogen or a substituent radical containing from 1 to 18 carbon atoms; wherein each X represents a divalent radical selected from the group consisting of alkylene, alkylene-oxy-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a —$CR^5R^6$-divalent bridging group and each $R^5$ and $R^6$ radical individually represents hydrogen or a methyl radical; and wherein each n individually has a value of 0 or 1. The improvement in the process of said concurrently filed U.S. patent application comprises carrying out the process in the presence of minor amount of a catalytic activity enhancing additive present in the hydroformylation reaction medium of the process. The additive is selected from the class consisting of added water, a weakly acidic compound (e.g. a compound having a pKa value of from about 1.0 to about 12), or both added water and a weakly acidic compound. The weak acidic compounds useful in the process of said concurrency filed U.S. patent application include biphenol (also called 2,2′-dihydroxy biphenyl or 2,2′-biphenol). In a preferred embodiment of the present invention, an additive of said concurrently filed U.S. patent application is also used along with the above described epoxides.

The hydroformylation reaction conditions that may be employed in the hydroformylation process encompassed by this invention may include any suitable continuous hydroformylation conditions heretofore disclosed in the above-mentioned patents. For instance, the total gas pressure of hydrogen carbon monoxide and olefinic unsaturated starting compound of the hydroformylation process may range from about 1 to about 10,000 psia. In general, however, it is preferred that the process be operated at a total gas pressure of hydrogen, carbon monoxide and olefinic unsaturated starting compound of less that about 1500 psia and more preferably less than about 500 psia. The minimum total pressure being limited predominately by the amount of reactants necessary to obtain a desired rate of reaction. More specifically the carbon monoxide partial pressure of the hydroformylation process of this invention is preferable from about 1 to about 120 psia, and more preferably from about 3 to about 90 psia, while the hydrogen partial pressure is preferably about 15 to about 160 psia and more preferably from about 30 to about 100 psia. In general $H_2:CO$ molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150°. In general hydroformylation reaction temperature of about 50° C. to about 120° C. are preferred for all types of olefinic starting materials, the more preferred reaction temperatures being from about 50° C. to about 100° C. and most preferably about 80° C.

The olefinic starting material reactants that may be employed in the hydroformylation process encompassed by this invention include olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isobutene, etc. (such as so called dimeric, trimeric or tetrameric propylene and the like, as disclosed, e.g., in U.S. Pat. Nos. 4,518,809 and 4,528,403). Moreover, such olefinic compounds may further contain one or more ethylenic unsaturated groups, and of course, mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,668,651 and the like.

Illustrative olefinic unsaturated compounds are alpha-olefins, internal olefins, alkyl alkenoates, alkenyl alkanoates, alkenyl alkyl ethers, alkenols, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene,1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta- pinene, dicyclopentadiene, cyclooctadiene, camphene, linalool, and the like.

Mixtures of different olefinic starting materials can be employed, if desired, in the hydroformylation process of the present invention. More preferably the subject invention is especially useful for the production of aldehydes, by hydroformylating alpha olefins containing from 2 to 20 carbon atoms, including isobutylene, and internal olefins containing from 4 to 20 carbon atoms as well as starting material mixtures of such alpha olefins and internal olefins. Commercial-alpha olefins containing four or more carbon atoms may contain minor amounts of corresponding internal olefins and/or their corresponding saturatedhydrocarbon and that such commercial olefins need not necessarily be purified from same prior to being hydroformylated.

The hydroformylation process of this invention involves the use of a rhodium-phosphite ligand complex catalyst as described herein. Of course mixtures of such catalysts can also be employed if desired. The amount of rhodium-phosphite complex catalyst present in the reaction medium of a given hydroformylation process encompassed by this invention need only be that minimum amount necessary to provide the given rhodium concentration desired to be employed and which will furnish the basis for at least the catalytic amount of rhodium necessary to catalyze the particular hydroformylation process involved such as disclosed e.g. in the above-mentioned patents. In general, rhodium concentrations in the range of from about 10 ppm to about 1000 ppm, calculated as free rhodium, in the hydroformylation reaction medium should be sufficient for most processes, while it is generally preferred to employ from about 10 to 500 ppm of rhodium and more preferably from 25 to 350 ppm to rhodium.

In addition to the rhodium-phosphite ligand complex used as the catalyst in the preferred hydroformylation process of this invention, free phosphite ligand (i.e., ligand that is not complexed with the rhodium metal) can also be employed. The free phosphite ligand may correspond to any of the above-defined phosphite ligands discussed above as employable herein. When employed, it is preferred that the free phosphite ligand be the same as the phosphite ligand of the rhodium-phosphite complex catalyst employed. However, such ligands need not be the same in any given process. Moreover, while it may not be absolutely necessary for the hydroformylation process to be carried out in the presence of any such free phosphite ligand, the presence of at least some amount of free phosphite ligand in the hydroformylation reaction medium is preferred. Thus the hydroformylation process of this invention may be carried out in the absence or presence of any amount of free phosphite ligand, e.g. up to 100 moles, or higher per mole of rhodium metal in the hydroformylation reaction medium. Preferably the hydroformylation process of this invention is carried out in the presence of from about 1 to about 50 moles of phosphite ligand, and more preferably from about 1 to about 4 moles of phosphite ligand, per mole of rhodium metal present in the reaction medium; said amounts of phosphite ligand being the sum of both the amount of phosphite ligand that is bound (complexed) to the rhodium metal present and the amount of free (non-complexed) phosphite ligand present. Of course, if desired, make-up or additional phosphite ligand can be supplied to the reaction medium of the hydroformylation process at any time and in any suitable manner, e.g. to maintain a predetermined level of free ligand in the reaction medium.

The hydroformylation process encompassed by this invention are also conducted in the presence of an organic solvent for the rhodium-phosphite complex catalyst and any free phosphite ligand that might be present. Any suitable solvent which does not unduly adversely interfere with the intended hydroformylation process can be employed. Illustrative suitable solvents for rhodium-catalyzed hydroformylation processes include those disclosed e.g. in U.S. Pat. No. 4,668,651. Mixtures of one or more different solvents may be employed if desired. Most preferably the solvent will be one in which the olefinic starting material, catalyst, and weakly acidic additive if employed, are all substantially soluble. In general, it is preferred to employ aldehyde compounds corresponding to the aldehyde products desired to be produced and/or higher boiling aldehyde liquid condensation by-products as the primary solvent, such as the higher boiling aldehyde liquid condensation by-products that are produced in situ during the hydroformylation process. Indeed, while one may employ any suitable solvent at the start up of a continuous process, the primary solvent will normally eventually comprise both aldehyde products and higher boiling aldehyde liquid condensation by-products due to the nature of such continuous processes. Such aldehyde condensation by-products can also be preformed if desired and used accordingly. The amount of solvent employed is not critical to the subject invention and need only be that amount sufficient to provide the reaction medium with the particular rhodium concentration desired for a given process. In general, the amount of solvent may range from about 5 percent by weight up to about 95 percent by weight or more based on the total weight of the reaction medium.

The hydroformylation process of this invention preferably involves a liquid catalyst recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures it is commonplace to continuously remove a portion of the liquid reaction product medium, containing, e.g., the aldehyde product, the solubilized rhodium-phosphite complex catalyst, free phosphite ligand, and organic solvent, as well as by-products produced in situ by the hydroformylation, e.g., aldehyde condensation by-products etc., and unreacted olefinic starting material, carbon monoxide and hydrogen (syn gas) dissolved in said medium, from the hydroformylation reactor, to a distillation zone, e.g., a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains rhodium-phosphite complex catalyst, solvent, free bisphosphite ligand and usually some undistilled aldehyde product is then recycled back, with or without further treatment as desired, along with whatever by-product and non-volatilized gaseous reactants that might still also be dissolved in said recycled liquid residue, in any conventional manner desired, to the hydroformylation reactor, such as disclosed e.g. in the above-mentioned patents. Moreover the reactant gases so removed by such distillation from the vaporizer may also be recycled back to the reactor if desired.

The distillation and separation of the desired aldehyde product from the rhodium- phosphite complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium and then pass said volatilized gases and liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures or below on up to total gas pressure of about 50 psig should be sufficient for most purposes.

Although the present invention has been described above with reference to olefin hydroformylation, it is broadly applicable to other reactions catalyzed by transition metal-phosphite ligand complexes (other than epoxide hydroformylation). By way of illustration, this invention is applicable to hydrogenating unsaturated compounds [such as copolymers of a conjugated diene and co-polymerizable monomer(s)] as disclosed in U.S. Pat. Nos. 4,464,515 and 4,503,196; oligomerizing or dimerizing olefins as disclosed in European Patent Applications 366212 and 177999; synthesizing optically-active pharmaceuticals as disclosed in U.S. patent application Ser. No. 911,518, filed July 16, 1992; hy-drocyanating butadiene to adiponitrile as disclosed in U.S. Pat. Nos. 4,810,815 and 4,714,773; decarbonylating aldehydes as disclosed in F. Abu-Hassanayn, M. E. Goldman, A. S. Goldman, J. Am. Chem. Soc. 114 (7), 2520, (1992) and R. B. King, Synlett (10), 671, (1991) and hydrosilylating olefins as disclosed in U.S. Pat. No. 5,103,033 and in European Pat. No. Application 459464. The disclosures of the above-mentioned patents, articles and patent applications relating to the specific reactants and reaction conditions are incorporated herein by reference.

The following Examples illustrate the process of the invention without limiting it in any way.

In the following Examples, the abbreviations used have the indicated meanings:
gmols/L/Hr gram moles per liter-hour
wppm parts per million on a weight basis
wt weight
psig pounds per square inch gauge pressure
psig pounds per square inch absolute pressure
conc. concentration
$^{31}$PNMR Nuclear Magnetic Resonance Spectroscopy based on phosphorus having an atomic mass of 31.
Diepoxide A 3,4-epoxycyclohexylmethyl-3,4-epoxycyclohexane-carboxylate
Ligand A The name and the formula of this bisphosphite ligand are given above.

GENERAL PROCEDURE FOR PREPARATION AND TESTING OF SOLUTIONS ("GENERAL PROCEDURE")

To provide comparable solutions upon which a plurality of parallel experiments could be carried out to illustrate the present invention, a phosphite ligand-containing catalyst solution was prepared and divided into several aliquots. The solution contained Ligand A, biphenol, rhodium dicarbonylacetylacetonate and n-butyraldehyde. Each aliquot was treated under different conditions as described in Examples 1 to 7 below. The conditions constituted a severe test of the stability of phosphite ligands and served as a screening technique to identify useful epoxides for ligand stabilization. These Examples illustrate that he method of this invention is effective in stabilizing phosphite ligands.

Aliquots of phosphite ligand-containing catalyst solution were separately charged to nitrogen flushed batch containers. The solution in the first container or testing unit did not contain any epoxide and served as a control for assessing a normal rate of hydrolysis for the unstabilized phosphite ligand-containing catalyst. Hydroxyalkylphosphonic acids are byproducts formed in the decomposition of Ligand A in hydroformylation reaction solutions and catalyze the autocatalytic decomposition of Ligand A. Hence to the solution in the second container or testing unit was added hydroxyalkylphosphonic acid and water to simulate the onset of autocatalytic hydrolysis. The rate and extent of hydrolysis was determined at the conclusion of the test period. To the remaining aliquots were added, not only with hydroxyalkylphosphonic acid and water, but also epoxides (as identified in each Example) to stabilize the ligand.

Each container into which catalyst solution was charged then was purged with nitrogen and was pressurized to approximately 60 psig with synthesis gas (i.e., a gaseous composition comprising about 50 percent hydrogen and 50 percent carbon monoxide.) The temperature of the contents of the container then was raised to about 110° C. and the contents were maintained at that temperature for 24 hours. Periodic gas chromatographic analysis of each reaction solution was utilized to determine the extent of hydrolysis of the phosphite ligand by determining the quantity of ligand remaining in the solution.

In Examples 1 to 7 below, the above-described General Procedure was used under conditions that simulated hydroformylation conditions, except that no olefin was present and so no hydroformylation occurred and no aldehyde was formed.

EXAMPLE 1

A simulated hydroformylation reaction solution was containing 72 wppm rhodium, 0.6 wt percent of Ligand A, about 84 wt percent butyraldehyde about 8.2 wt percent tetraglyme (tetraethylene glycol dimethyl ether) as a solvent and about 7.1 wt percent biphenol. Five equal aliquots of this solution were charged to separate nitrogen-purged containers (Fisher Porter bottles).

Sample A was left unchanged to serve as a control for assessing the normal phosphite ligand hydrolysis rate. To each of the other Samples (Samples B through E), was added 0.2 wt percent hydroxypentylphosphonic acid and 0.6 wt percent water, each based on the total weight of the contents of the container. No epoxide was added to Sample B, whereas 5 weight percent cyclohexene oxide was added to Sample C, 5 weight percent styrene oxide was added to Sample D and 5 weight percent propylene oxide was added to Sample E. The solutions were tested as set out in the above-described General Procedure to simulate hydroformylation reaction conditions. However, since no olefin was present, no hydroformylation occurred.

Samples of the solution were taken periodically to determine the amount of ligand remaining in the solutions. Table 1 below indicates the percentage of the original ligand remaining after 24 hours. The results with Samples C, D and E illustrate the improvements that are achieved by the practice of the present invention.

TABLE 1

| Sample | Original Ligand (Wt. % Remaining) |
|---|---|
| 1A | 100 |
| 1B | 0 |
| 1C | 97 |
| 1D | 34 |
| 1E | 39 |

In Examples 2 to 7 below, controls similar to Samples A and B of Example 1 above were prepared and tested with results similar to the results shown in Table 1 for Samples A and B. For the sake of brevity, such preparations and testing of controls are omitted from the description of Examples 2 to 7 below.

EXAMPLE 2

Simulated hydroformylation reaction solutions comprising 71 wppm rhodium, Ligand A in a quantity sufficient to yield a reaction mixture having a ligand concentration of 0.6 wt percent and 69 wt percent butyraldehyde were mixed with 0.2 wt percent hydroxypentylphosphonic acid, 0.6 wt percent water and cyclohexene oxide at the concentrations set forth in Table 2. The solutions were tested as set out in the above-described General Procedure. The data in Table 2 illustrate the effect of epoxide concentration on phosphite ligand stability after 24 hours.

TABLE 2

| Sample | Epoxide Concentration (Wt. %) | Original Ligand Remaining (Wt. %) |
|---|---|---|
| 2C | 3.0 | 100 |
| 2D | 1.0 | 81 |
| 2E | 0.5 | 11 |
| 2F | 0.1 | 0 |

EXAMPLE 3

A simulated hydroformylation reaction solution was formed comprising 75 wppm rhodium, Ligand A in a quantity sufficient to yield a reaction mixture having a ligand concentration of 0.6 wt percent and 70 wt percent butyraldehyde to separate portions of the solution were added with hydroxypentylphosphonic acid, water, and cyclohexene oxide at the concentrations set forth in Table 3. The solutions were tested as set out in the above-described General Procedure. The data in Table 3 illustrate the effect of epoxide concentration and acid concentration on phosphite ligand stability after 24 hours.

TABLE 3

| Sample | HPPA[1] (wt. %) | Water (wt. %) | Epoxide Conc., (wt. %) | Ligand Remaining (Wt. %) |
|---|---|---|---|---|
| 3C | 0.01 | 7.5 | 0.2 | 100+ |
| 3D | 0.02 | 7.5 | 0.2 | 89 |
| 3E | 0.005 | 2.5 | 0.05 | 99 |
| 3F | 0.01 | 7.5 | 0.05 | 94 |

Note 1:
HPPA means hydroxypentylphosphonic acid.

EXAMPLE 4

A simulated hydroformylation reaction solution was formed comprising 72 wppm rhodium, Ligand A in a quantity sufficient to yield a reaction mixture having a ligand concentration of 0.6 wt percent, and 70 wt percent butyraldehyde. Then 0.01 wt percent hydroxypentylphosphonic acid, 2.5 wt percent water and 0.02 wt percent cyclohexene oxide were added to the solution. The solution was tested as set out in the above-described General Procedure. The solution had retained 97 wt percent of the original ligand concentration.

EXAMPLE 5

A simulated hydroformylation reaction solution was formed comprising 70 wppm rhodium, Ligand A in a quantity sufficient to yield a reaction mixture having a ligand concentration of 0.6 wt percent and 83 wt percent butyraldehyde. To the solution were added 0.2 wt percent hydroxypentylphosphonic acid, 0.6 wt percent water and 5 wt percent 2,3-epoxynorbornane. The solution was tested as set out in the above-described General Procedure. The solution retained 83 wt percent of the original ligand concentration.

EXAMPLE 6

A simulated hydroformylation reactant solution was formed comprising 72 wppm rhodium, Ligand A in quantities sufficient to yield reaction mixtures having ligand concentrations as set forth in Table 6 and 85 wt percent butyraldehyde. To separate portions of the solution were added 0.3 wt percent hydroxypentylphosphonic acid, 0.7 wt percent water and epoxides of the type and at the concentrations set forth in Table 6. The solutions were tested as set out in the above-described General Procedure. The data in Table 6 illustrate the effect of epoxide concentration and epoxide identity on phosphite ligand stability after 24 hours.

TABLE 6

| Sample | Initial Ligand Conc. (wt. %) | Epoxide Type* | Epoxide Conc. (wt. %) | Original Ligand Remaining (Wt. %) |
|---|---|---|---|---|
| 6C | 0.467 | C8 | 5.7 | 79 |
| 6D | 0.416 | C12 | 5.7 | 83 |
| 6E | 0.307 | CyC12 | 5.7 | 44 |
| 6F | 0.165 | C10 | 5.0 | 70 |
| 6G | 0.160 | C16 | 5.0 | 88 |
| 6H | 0.140 | C18 | 5.0 | 89 |

*The following is the key for the identities of the epoxides:
C8 1,2-octene oxide
C12 1,2-dodecene oxide
CyC12 1,2-cyclododecene oxide
C10 1,2-decene oxide
C16 1,2-hexadecene oxide
C18 1,2-octadecene oxide

EXAMPLE 7

Simulated hydroformylation reactant solutions were formed comprising rhodium in concentrations as set forth in Table 7, Ligand A in quantities sufficient to yield reaction mixtures having ligand concentrations set forth in Table 7 and solvents in quantities as set forth in Table 7. To the solutions were added 0.3 wt percent hydroxypentylphosphonic acid, 1.5 wt percent water and 3.0 wt percent cyclohexene oxide. The solutions were tested as set out in the above-described General Procedure. The data in Table 7 illustrate the effect of differences in solution composition on phosphite ligand stability after 24 hours.

TABLE 7

| Sample | Rh, (wppm) | Initial Ligand Conc. (wt. %) | Solvent Type* | Solvent Conc. (wt. %) | Final Ligand Conc. (wt. %) | Original Ligand Remaining (wt. %)** |
|---|---|---|---|---|---|---|
| 7C | 762 | 7.1 | Tol | 88 | 7.7 | 117 |
| 7D | 0 | 7.8 | Tol | 88 | 8.3 | 106 |
| 7E | 74 | 0.64 | TG | 89 | 0.64 | 100 |
| 7F | 750 | 6.4 | Tol | 88 | 6.0 | 94 |

TABLE 7-continued

| Sample | Rh, (wppm) | Initial Ligand Conc. (wt. %) | Solvent Type* | Solvent Conc. (wt. %) | Final Ligand Conc. (wt. %) | Original Ligand Remaining (wt. %)** |
|---|---|---|---|---|---|---|
| 7G | 74 | 2.9 | THF | 89 | 3.0 | 103 |

*The following is the key for the identities of the solvents:
Tol: Toluene
TG: Tetraglyme
THF: Tetrahydrofuran
**Indication of ligand recovery of greater than 100 percent reflects experimental error. In each sample, therefore, it can reasonably be stated that essentially all of the original ligand was present after 24 hours.

EXAMPLE 8

Reactant solutions comprising 250 wppm rhodium and Ligand A at a concentration of 2.5 wt percent was utilized to catalyze the hydroformylation of propylene in a continuous testing apparatus in side-by-side continuous testing units. Each continuous testing unit comprised a three-ounce pressure bottle submerged in an oil bath with a glass front (for viewing). Homogeneous catalysis was allowed to proceed in each testing unit until the rate of hydroformylation had reached steady state.

The catalyst solution (20 grams) was charged to the bottle with a syringe after the bottle had been purged with nitrogen. The bottle was closed, and was again purged with nitrogen. The oil bath was heated to the desired hydroformylation reaction temperature (100° C.).

The hydroformylation reaction was conducted in the bottles at about 45 psia partial pressures of hydrogen and carbon monoxide and propylene at 10 psia, respectively. Flows of feed gases (nitrogen, carbon monoxide, hydrogen, and olefin) to the bottles were controlled individually with mass flow meters and the feed gases dispersed into the catalyst solution through frited spargers. The hydroformylation rate reached steady state in about one week.

One of the bottles served as a control (Sample 8A). To each of the other bottles (Samples 8B to 8E) was added 0.005 parts by weight of hydroxypentylphosphonic acid and 0.05 parts by weight of water to simulate acid formation. Two of these bottles (Samples 8B and 8D) were not treated with epoxide and hydroformylation was allowed to proceed until the ligand had undergone essentially complete autocatalytic degradation. Two of the other acid-and water-treated bottles (Samples 8C and 8E) were charged further with 0.015 grams of weight cyclohexene oxide and 0.3 grams of dodecene oxide, respectively.

The data in Table 8 illustrate the effectiveness of the epoxide treatment in accordance with the method of the invention. Untreated Sample 8A showed essentially no decline in the ratio (R) of the hydroformylation rate to the propylene partial pressure after an 8 day period. The test on Sample 8A was conducted without the addition of acid, epoxide or water. The results with Sample 8A show that it is necessary to introduce hydroxyalkylphosphonic acid and water to induce autocatalytic degradation in the short periods involved in the tests conducted in this Example. Sample 8C (acid, water and cyclohexene oxide added) showed no decline in the value of R and Sample 8E (acid, water and dodecene oxide added) showed an increase in R after 5 days. Both of the samples to which no epoxide had been added but to which both acid and water had been added (i.e., Samples 8B and 8D) suffered essentially complete loss of catalytic activity, as indicated by R values of essentially zero, after only 5 days.

TABLE 8

| Sample | Initial R | Final R | Duration of Evaluation, (days) |
|---|---|---|---|
| A | 0.4 | 0.4 | 8 |
| B | 0.4 | 0.0 | 5 |
| C | 0.4 | 0.4 | 8 |
| D | 0.46 | 0.02 | 5 |
| E | 0.46 | 0.56 | 5 |

Examples 9 and 10 below indicate that the actual hydroxyalkane phosphonic acid "sequestering agent" during hydroformylation in accordance with the hydroformylation process of the present invention is the epoxide and not the aldehyde formed by the hydroformylation. The production of dioxolanes by the reaction of the phosphonic acid degradation product and the aldehyde might have been expected in view of the disclosure of S. B. Lee, T. Takata, T. Endo, Chem. Left., (II), 2019–22, (1990). These Examples also suggest that the "sequestration" of such acids (e.g., 1-hydroxyalkane phosphonic acid) by the epoxide is catalyzed by some component of the hydroformylation reaction medium since reaction of the 1-hydroxylbutyl phosphonic acid with the epoxide did not occur by simply contacting the phosphonic acid with the epoxide in the aldehyde.

EXAMPLE 9

A 200 mL round bottom flask equipped with a magnetic stirring bar was charged with a solution of 0.86 g. of 1-hydroxyamylphosphonic acid, 1.97 g. of 1,2-epoxydodecane and 51 g. of n-valeraldehyde. No new phosphorus compounds were detected by $^{31}$PNMR after stirring for two weeks at room temperature. After an additional week at room temperature, there was no apparent reaction between the 1-hydroxyamylphosphonic acid and 1,2-epoxydodecane as ascertained from the $^{31}$PNMR. The reaction mixture was then washed three times with 5% sodium bicarbonate solution. The extractate contained no phosphorus component evident in the $^{31}$PNMR. The extractate was washed once with distilled water, dried over anhydrous magnesium sulfate and stripped on a rotary evaporator to give a colorless oil weighing 10.1 g. A major high boiling component of this solution, as determined by gas chromatographic mass spectroscopy was 2-n-amyl-4-n-decyl-1,3-dioxolane. These results indicate that no apparent reaction of 1-hydroxyamylphosphonic acid with 1,2-epoxydodecane occurs under conditions where 1,2-epoxydodecane reacts with the n-valeraldehyde to form 2-n-butyl-4-n-decyl-1,3-dioxolane.

EXAMPLE 10

A glass reactor Fisher Porter TM pressure vessel was charged with 20 mL of a catalyst solution containing 0.025 parts rhodium (as rhodium dicarbonyl-1,3-pentanedionate), 2.5 parts Ligand A, 2 parts 2,2'-biphenol, and 95.475 parts tetraglyme. Propylene, carbon monoxide and hydrogen were passed through the catalyst solution to maintain average partial pressures of 3.1, 44, and 44 psia, respectively. Nitrogen gas was fed to the reactor to maintain a total reactor pressure of 165 psig. After 48 hours operation, 1 mL of tetraglyme solution containing 0.5 parts 1-hydroxybutyl-phosphonic acid and 5 parts water was added and then 1.3 mL of an n-butyraldehyde solution containing 0.64 g. 2-n-butyl-4-n-decyl-1,3-dioxolane was added to the reactor. No appreciable hydrolysis had occurred after 24 hours operation as determined by $^{31}$PNMR. Then additional portions of 1-hydroxylbutylphosphonic acid and the dioxalane were added in amounts equivalent to those added initially. After an additional 24 hours operation, the reactor was monitored by $^{31}$PNMR. Approximately, 52% of the ligand had been converted into hydrolysis products. These results indicate the ineffectiveness of 2-n-amyl-4-n-decyl-1,3-dioxolane in suppressing hydroxybutyl phosphonic acid-catalyzed hydrolysis of Ligand A during hydroformylation.

EXAMPLE 11

This Example illustrates the use of 1,2-epoxydodecane to suppress the autocatalytic hydrolysis of Ligand A. A glass reactor was charged with 20 mL of a catalyst solution having the same composition as the solution used in Example 10 above. Propylene, carbon monoxide and hydrogen were introduced into the solution. The average propylene, carbon monoxide, and hydrogen partial pressures were 4.0, 46 and 46 psia, respectively. Nitrogen gas was fed to the reactor to maintain a total reactor pressure of 165 psig. After forty eight hours operation, a solution of 1-hydroxybutylphosponic acid in aqueous tetraglyme was added and then a solution of 1,2-epoxydodecane in n-butyraldehyde was added to the reactor. After an additional 24 hours of operation, addition of the acid and the epoxide was repeated. After another 24 hours, the $^{31}$PNMR of the solution showed that the ligand was approximately 16% hydrolyzed.

EXAMPLE 12

A mixed olefin starting material [butene-1 and butene-2 (cis and trans)] was hydroformylated for 124 days as follows: A liquid recycle reactor system was employed which contained two 2.8 liter stainless steel stirred tank reactors (Reactors 1 and 2) connected in series. Each reactor had a vertically mounted agitator and a circular tubular sparger near the bottom for feeding the olefin and/or syn gas to the reactor. The sparget contained a plurality of holes of sufficient size to provide the desired gas flow into the liquid body. Each reactor contained a silicone oil shell as means of bringing the contents of the reactor up to reaction temperature and each reactor contained internal cooling coils for controlling the reaction temperature. Reactors 1 and 2 were connected via a line to transfer any unreacted gases from Reactor 1 to Reactor 2 and were further connected via a line so that a portion of the liquid reaction solution containing aldehyde product and catalyst from Reactor 1 could be pumped into Reactor 2. Hence the unreacted olefin of Reactor 1 was further hydroformylated in Reactor 2.

Each reactor also contained a pneumatic liquid level controller for automatic control of the liquid levels in the reactors. Reactor 1 further contained a line for introducing the olefin, carbon monoxide and hydrogen through the sparger while make up carbon monoxide and hydrogen was added to Reactor 2 via a transfer line that also carried the unreacted gases from Reactor 1 to Reactor 2. Reactor 2 also contained a blow-off vent for removal of the unreacted gases. A line from the bottom of Reactor 2 was connected to the top of a vaporizer so that a portion of the liquid reaction solution could be pumped from Reactor 2 to the vaporizer. Vaporized aldehyde was separated from the non-volatilized components of the liquid reaction solution in the gas-liquid separator part of the vaporizer. The remaining non-volatilized solution was pumped through a recycle line back into Reactor 1. The recycle line also contained a pneumatic liquid level controller. The vaporized aldehyde product was passed into a water cooled condenser, liquified and collected in a product receiver.

The hydroformylation reaction was conducted by charging to Reactor 1 one liter of catalyst precursor solution comprising rhodium dicarbonyl acetylacetonate (about 125 ppm rhodium), about 0.75% of Ligand A (about 7.4 mole equivalents of Ligand A per rhodium), 3.75% of 2,2'-biphenol and, as solvent, about 10% of tetraethylene glycol dimethyl ether and about 85.5% of $C_5$ aldehyde (n-valeraldehyde and 2-methylbutyraldehyde in the ratio of about 30:1). Reactor 2 was charged with the same amounts of the same precursor solution. The reactors were then purged with nitrogen to remove any oxygen present. Then about 100 psig of nitrogen pressure was put on both reactors and the reactors were heated to the reaction temperatures shown in the Table 9. Controlled flows of purified hydrogen, carbon monoxide and a mixed butenes [1-butene and butene-2 (cis and trans)] were fed through the sparget into the bottom of Reactor 1 and the reactor pressure was increased to the operating pressure given in the Table 9. When the liquid level in Reactor 1 started to increase as a result of liquid aldehyde product formation, a portion of the liquid reaction solution was pumped from Reactor 1 to Reactor 2 through a line at the top of Reactor 2 at a rate sufficient to maintain a constant liquid level in Reactor 1. The pressure of Reactor 2 increased to its operating pressure given in the Table 9. Blow-off gas from Reactor 2 was collected and measured. A controlled flow of make-up syn gas (CO and $H_2$) was added to Reactor 2 in order to maintain their desired partial pressures in Reactor 2. The above-mentioned operating pressures and reaction temperatures were maintained throughout the hydroformylation. As the liquid level in Reactor 2 started to increase as a result of liquid aldehyde product formation, a portion of the liquid reaction solution was pumped to the vaporizer/separator at a rate sufficient to maintain a constant liquid level in Reactor 2. The crude aldehyde product was separated at 109° C. and 24.7 psia from the liquid reaction solution, condensed and collected in a product receiver. The non-volatized catalyst-containing liquid reaction solution remaining in Reactor 2 was recycled back to Reactor 1.

Every third day over the course of the 124 day run, 2 milliliters of 1,2-epoxydodecane was fed into each of Reactors 1 and 2 via a valve fitted with a septum in the bottom of each reactor to give an epoxide concentration after each addition of about 0.2% in each reactor.

The hydroformylation of the mixed butene feed was continued for 124 days. The hydroformylation reaction conditions as well as the rate of $C_5$ aldehydes produced (in terms of gram moles per liter per hour) and the linear to branched aldehyde product ratio (n-valeraldehyde to 2-methlybutyraldehyde) are shown in the Table 9. The activity of the catalyst was constant over the 124 day course of the run as shown in the Table 9. This constant activity indicates that excessive ligand degradation had not occurred over the course of the run.

TABLE 9

| Days of Operation | 2 | 21 | 41 | 81 | 124 |
|---|---|---|---|---|---|
| Reactor 1 | | | | | |
| °C. | 85 | 85 | 85 | 85 | 85 |
| $H_2$, psia | 79.8 | 88.4 | 83.1 | 98.1 | 99 |
| CO, psia | 90.9 | 91.5 | 88.5 | 81.6 | 89.1 |
| 1-$C_4H_8$, psia | 6.4 | 10.5 | 14.8 | 7.5 | 5.4 |
| 2-$C_4H_8$, psia | 42.3 | 27.6 | 35.2 | 36 | 36.9* |
| Reactor 2 | | | | | |
| °C. | 90 | 95 | 85 | 85 | 85 |
| $H_2$, psia | 68.6 | 78.8 | 74.5 | 74.7 | 96.7 |
| CO, psia | 87.3 | 81.7 | 85.2 | 87.3 | 84.7 |
| 1-$C_4H_8$, psia | 0.8 | 1 | 1.5 | 1.2 | 1.1 |
| 2-$C_4H_8$, psia | 31.9 | 23 | 29.4 | 30.3 | 33.7** |
| Results | | | | | |
| $C_5$ aldehydes, gmols/L/Hr | 1.489 | 1.706 | 1.751 | 1.847 | 1.832 |
| Linear/branched aldehyde ratio | 32.3 | 31.2 | 30.3 | 35.9 | 30.0 |

*There was an average pressure of 16.2 psia in Reactor 1 due to the cis isomer and an average pressure of 14.3 psia due to trans isomer over the 124 days of the run
**There was an average pressure of 16.9 psia in Reactor 2 due to the cis isomer and an average pressure of 11.9 psia due to trans isomer over the 124 days of the run

EXAMPLE 13

Following the procedure set out in Example 12 above, two reactors were employed in series to hydroformylate mixed butenes. The same partial pressures of the reactant gases were employed and the same concentrations of rhodium and ligand were used as in Example 12 above. This run differed from the run of Example 12 in the employment of a Diepoxide A in place of the 1,2-epoxydodecane as the stabilizing additive. The rate of formation of $C_5$ aldehyde products on the first day of this run was 2.11 gmols/L/Hr and the rate of formation of aldehyde products on the twenty-second day of this run was 1.71 gmols/L/Hr. There was no evidence of significant ligand degradation over this period of operation.

EXAMPLE 14

In a continuous catalyst liquid recycle manner, propylene was hydroformylated for 52 days using a single reactor. A liter of catalyst solution comprising rhodium dicarbonyl acetylacetonate (about 102 ppm rhodium), about 0.6 wt. % of 6,6'[[3,3',5,5'-tetrakis(1,1-dimethylethyl) 1,1'-biphenylk-2,2'diyl]bis(oxy)]bis-dibenzo[d,f] [1,3,2]-dioxaphosphepin ligand [Ligand A] (about 7.2 mole equivalents of Ligand A per mole equivalent of rhodium), and, as solvent, about 12 wt. % of tetraethylene glycol dimethyl ether (tetraglyme) and about 85.4 wt. % of $C_4$ aldehyde (n-butyraldehyde and iso-butyraldehyde in the ratio of about 25–30:1) was employed. Water was also added to the reaction system at a rate of about 1000 ppm by weight on a synthesis gas (CO+$H_2$) basis in the form of water saturated synthesis gas by sparging a third of the syn gas employed through a tank of water before adding it to the reactor. The water concentration in the reaction solution of the reactor averaged around 0.2 wt. %, although the standard deviation was higher than normal. Subsequent similar experiments were carried out wherein the water concentration was about 0.2 weight percent. An amount equal to 0.07 volume percent of 1,2-epoxydodecane was added three times per week to stabilize the ligand. No other additive was added to the reaction medium.

The hydroformylation of the propylene feed was continued for 52 days. The hydroformylation reaction conditions as well as the rate of butyraldehydes produced (in terms of gram moles of aldehyde product per liter of catalyst solution per hour of reaction) and the linear to branched aldehyde product ratio (n-butyraldehyde to iso-butyraldehyde) are shown in Table 10.

TABLE 10

| | Average | Range |
|---|---|---|
| Days Operation | 52.5 | — |
| Operating Reactor Conditions | | |
| Pres., psia | 175.7 | 184.7–106.7 |
| Temp., °C. | 85.0 | — |
| Rhodium Conc. ppmw | 61 | 47–71 |
| Ligand Conc., wt % | 0.39 | 0.51–0.29 |
| Aldehyde Conc., wt % | 85.2 | 90–80 |
| CO Partial Pressure, psi | 53.4 | 60–30 |
| $H_2$ Partial Pressure, psi | 53.3 | 63–30 |
| $C_3H_6$ Partial Pressure, psi | 40 | 53–22 |
| Operating Vaporizer Conditions | | |
| Temp., °C. | 104.5 | 100–125 |
| Pres., psi | 23.5 | 25.7–22.2 |
| Feed/Tails Ratio | 3.75 | 8.9–2.2 |
| Average Catalyst Performance | | |
| Aldehyde Rate, gmole/L/hr | 3.6 | 4.1–3.1 |
| Isomer Ratio (n:iso) | 22.7 | 32–2.7 |
| Propane Selectivity, % | 2.3 | 2.7–1.3 |
| Heavies Selectivity, % | 0.05 | |
| Heavies Rate, g/L/hr | 0.2 | |

In above Example 14, after eight days of operation all the free ligand had been oxidized due to an inadvertent unknown source of oxygen. Loss of all the free ligand produced a sharp drop in aldehyde product isomer ratio and an increase in the observed activity of the catalyst. Fresh make-up ligand was added and the reaction unit began operation normally again without evidencing any rhodium loss. Synthesis gas partial pressures were periodically lowered briefly from 60 psi each to 30 psi each to check the kinetic responses of the gases. Ligand consumption during the run excluding the initial oxidation problem was 0.14 g/L/day. Phosphorus NMR of the catalyst solution showed no unusual behavior regarding ligand decomposition. Poisoning phosphite was not evident in the spectra following the first oxidation of the ligand. The vaporizer temperature was held at about 100° C. for most of the run and catalyst activity was steady. When the vaporizer temperature was increased to 115° C. a decline in catalyst activity was observed which increased sharply when the vaporizer temperature was increased to 125° C. These results demonstrate the effectiveness of the addition both of water as a catalytic activity enhancing additive for the hydroformylation process and of the addition of an epoxide to stabilize the ligand.

What is claimed is:

1. A process for stabilizing a phosphite ligand against degradation in a homogeneous hydroformylation reaction mixture containing an olefinic compound, carbon monoxide, hydrogen, a rhodium catalyst and the phosphite ligand, said process comprising adding to the reaction mixture a minor minor amount of an epoxide sufficient to reduce the degradation of the phosphite ligand, said amount of epoxide being in the range of from 0.001 to 5 weight percent based on the total weight of the reaction mixture.

2. The process of claim 1 wherein the ligand is selected from the group consisting of:

(i) poly-phosphites having the formula:

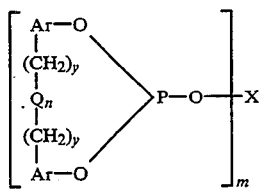
(I)

wherein:
(1) Ar represents an identical or different aryl group;
(2) X represents an m-valent hydrocarbon radical selected from the group consisting of alkylene, alkylene-oxy-alkylene, aryl and aryl-$(CH_2)_y$—$(Q)_n$—$(CH_2)_y$-aryl groups;
(3) each y individually has a value of 0 or 1;
(4) each Q individually represents a divalent bridging group selected from the class consisting of —$CR^1R^2$—, —O—, —S—, —$NR^3$—, —$SiR^4R^5$—, and —CO—;
wherein $R^1$ and $R^2$ each individually represents a group selected from the group consisting of hydrogen, alkyl of 1 to 12 carbon atoms, phenyl, tolyl and anisyl groups; and
$R^3$, $R^4$, and $R^5$ each individually represents —H or -an alkyl group
(5) each n individually has a value of 0 to 1; and
(6) m has a value of 2 to 6;

(ii) diorganophosphites having the formula:

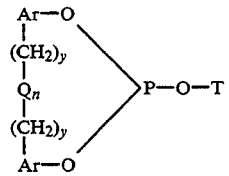
(II)

wherein T represents a monovalent hydrocarbon group; and wherein Ar, Q, n and y are as defined above; and (iii) open ended bis-phosphites having the formula:

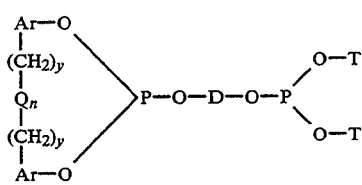
(III)

wherein D represents a divalent bridging group selected from the group consisting of alkylene, alkylene-oxy-alkylene, aryl, and aryl-$(CH_2)_y$—$Q_n$—$(CH_2)_y$-aryl and wherein At, Q, n, y and T are as defined above and each to may be identical or different; and (iv) triorganophosphites having the formula:

$(R^\circ O)_3 P$ (IV)

wherein $R^\circ$ is a substituted or unsubstituted monovalent hydrocarbon radical.

3. The process of claim 1 wherein the ligand is selected from the group consisting of:

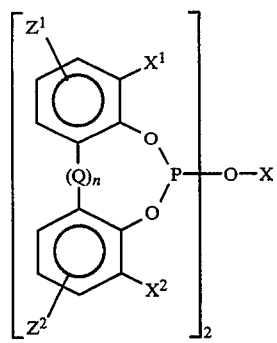

and

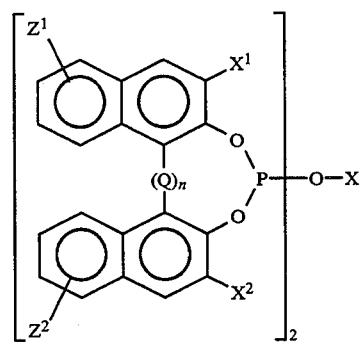

wherein each $X^1$ and $X^2$ radical individually represents a radical selected from the group consisting of hydrogen, methyl, ethyl and n-propyl; wherein each $Z^1$ and $Z^2$ radical individually represents hydrogen or a substituent radical containing from 1 to 18 carbon atoms; wherein each X represents a divalent radical selected from the group consisting of alkylene, alkylene-oxyalkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a —$CR^5R^6$-divalent bridging group and each $R^5$ and $R^6$ radical individually represents hydrogen or a methyl radical; and wherein each n individually has a value of 0 or 1.

4. The process of claim 1 wherein the degradation of the phosphite ligand is autocatalytic in the absence of the epoxide and the molar ratio of any acid in the reaction mixture to the transition metal is no greater than 0.05:1.

5. The process of claim 1 wherein the epoxide concentration in the reaction mixture is between about 0.01 to 2 weight percent based on the total weight of the reaction mixture.

6. The process of claim 1 wherein the epoxide concentration in the reaction mixture is between about 0.1 and 1.0 weight percent based on the total weight of the reaction mixture.

7. The process of claim 1 wherein the epoxide has the formula:

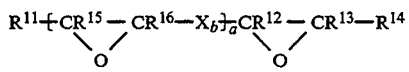

wherein
(1) a is 0 or 1;
(2) b is 0 or 1;
(3) $R^{11}$, $R^{12}$, $R^{13}$, $R^{14}$, $R^{15}$ and $R^{16}$ are independently selected from the group consisting of hydrogen; monovalent hydrocarbon radicals (such as alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$, $R^{12}$, $R^{13}$, $R^{14}$, $R^{15}$ and $R^{16}$ are linked together to form a cyclic structure which has up to about 30 carbon atoms and which may comprise a plurality of ring structures such as bicyclo-, tricyclo-, tetracyclo- and n-cyclo- groups; and
(4) X is a divalent bridging group selected from the group consisting of substituted or unsubstituted alkylene, arylene, aralkylene, and alkarylene groups having up to about 30 carbon atoms, —O—, —S—, —$NR^{19}$—, —$SiR^{20}R^{21}$, and —CO—, and wherein each radical $R^{19}$, $R^{20}$, and $R^{21}$ individually represents H or alkyl groups.

8. The process of claim 1 wherein the epoxide has the formula:

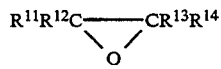

wherein $R^{11}$, $R^{12}$, $R^{13}$, $R^{14}$, $R^{15}$ and $R^{16}$ are independently selected from the group consisting of hydrogen; monovalent hydrocarbon radicals (such as alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$, $R^{12}$, $R^{13}$, $R^{14}$, $R^{15}$ and $R^{16}$ are linked together to form a cyclic structure which has up to about 30 carbon atoms and which may comprise a plurality of ring structures such as bicyclo-, tricyclo-, tetracyclo- and n-cyclo- groups.

9. The process of claim 1 wherein the epoxide is selected from the group consisting of cyclohexene oxide, 2,3-epoxynorbornane, 1,2-octene oxide, 1,2-dodecene oxide, 1,2-cyclododecene oxide, 1,2-decene oxide, 1,2-hexadecene oxide, 1,2-octadecene oxide, 1,2-cyclododecene oxide, 1,2-epoxydodecane, 2,3-epoxybutane and 3,4-epoxycyclohexylmethyl-3,4-epoxycyclohexane-carboxylate.

10. The process of claim 1 wherein the olefinic compound is propylene or a butene.

11. The process of claim 1 wherein the ligand is as defined in claim 3 and wherein the epoxide is defined as in claim 7.

12. The process of claim 1 wherein the ligand is as defined in claim 3 and wherein the epoxide is defined as in claim 8.

13. The process of claim 1 wherein the rhodium catalyst is being used to catalyze hydroformylation of propylene or butene by the reaction of the propylene or butene with carbon monoxide and hydrogen to produce an aldehyde, wherein the ligand is as defined in claim 3 and wherein the epoxide is defined as in claim 9.

* * * * *